United States Patent [19]

Hofmann

[11] Patent Number: 4,640,636
[45] Date of Patent: Feb. 3, 1987

[54] POWDER STICK WITH SHRINK FILM SHEATHING

[75] Inventor: Hans J. Hofmann, Nürnberg, Fed. Rep. of Germany

[73] Assignee: Schwan-Stabilo Schwanhäusser GmbH & Co., Nürnberg, Fed. Rep. of Germany

[21] Appl. No.: 712,641

[22] Filed: Mar. 18, 1985

[30] Foreign Application Priority Data

Feb. 15, 1985 [DE] Fed. Rep. of Germany ... 8504263[U]

[51] Int. Cl.⁴ .................. A45D 40/00; A45D 40/20
[52] U.S. Cl. ........................... 401/96; 401/49; 401/88
[58] Field of Search .......... 401/49, 88, 91, 96; 132/79 A, 79 C, 82 A, 88.5, 88.7; 53/557; 424/61, 63, 69, 64, DIG. 5; 128/DIG. 18

[56] References Cited

U.S. PATENT DOCUMENTS

| | | | |
|---|---|---|---|
| 2,390,473 | 12/1945 | Teichner | 401/96 |
| 3,471,611 | 10/1969 | Scott | 429/63 |
| 3,520,627 | 7/1970 | Suzuki | 401/96 |
| 3,669,095 | 6/1972 | Kobayashi et al. | 128/DIG. 18 |

FOREIGN PATENT DOCUMENTS 1461292  5/1969  Fed. Rep. of Germany ........ 401/96

Primary Examiner—Steven A. Bratlie

[57] ABSTRACT

Described is a powder stick which includes a shrink film sheathing thereon. The material of the shrink film sheathing is a plasticizer-free hard PVC film having a modulus of elasticity of from about 2400 to 3000 N/mm², with the shrink film being from about 50 to 200 μm in thickness.

6 Claims, 2 Drawing Figures

POWDER STICK WITH SHRINK FILM SHEATHING

BACKGROUND OF THE INVENTION

Various kinds of powder sticks for use in cosmetic pencils are known. In one such powder stick, as disclosed for example in German laid-open application (DE-OS) No 32 21 296, the powder stick is sheathed on its side surfaces by a shrink film or foil. Powder sticks of that kind are then made up into a suitable element for use for example as a cosmetic pencil by the powder stick being glued into a wood casing or a casing of other suitable material which can be appropriately sharpened to a point, for the purposes of applying the powder. The fact that the powder stick itself is sheathed by a shrink film gives the advantage that the stick is aptly substantially prevented from breaking up, thus reducing the reject rate in the operation of glueing the powder stick to the casing or in the operation of fitting the powder stick into a slide-type or rotary-type sleeve member or a sleeve comprising a material which can be sharpened to a point.

It has now been found that problems still arise, in spite of the powder stick being sheathed with a shrink film, more specifically for the reason that the shrink film under certain circumstances may be comparatively elastic so that the powder stick may suffer damage during handling thereof in subsequent processing operations, although such damage is not always visible from the exterior by virtue of the shrink film sheathing which bears closely and tightly against the powder stick. The fact that the actual powder stick has suffered damage becomes apparent only during use thereof, when the stick crumbles. That is obviously a serious problem with regard to quality control and consumer confidence. Furthermore, it must be possible easily to form a point on the stick, including the shrink film sheathing, and that is a factor which has also frequently caused difficulties with the shrink films which have been used hitherto as a sheathing on a powder stick. In more specific terms, the films are frequently torn during the operation of forming the point on the powder stick or the cosmetic pencil incorporating same, so that the protection afforded to the powder stick at its periphery, by the shrink film, was detrimentally affected, while also giving an unattractive appearance.

SUMMARY OF THE INVENTION

An object of the present invention is to provide a powder stick having a shrink film sheathing thereon, to provide substantially effective protection for the powder stick.

Another object of the present invention is to provide a powder stick having a shrink film sheathing thereon, which at least substantially reduces the danger of damage to the shrink film during further processing operations on the powder stick.

A further object of the present invention is to provide a powder stick which is sheathed with a shrink film having a substantial level of breaking strength.

A still further object of the present invention is to provide a shrink film-sheathed powder stick which can be substantially readily formed to a point for the purposes of powder application therefrom.

These and other objects are attained by a powder stick for a cosmetic pencil, which is sheathed on its side surface with a shrink film. The shrink film comprises plasticizer-free hard PVC having a modulus of elasticity of from about 2400 to 3000 N/mm$^2$ (in accordance with the German Industrial Standard DIN 53457), while being of a thickness of about 50 to 200 μm.

It is found that when a shrink film having the above-indicated characteristics is used as an enclosure means or sheathing for a powder stick, the result is that the sheathing is of comparatively high rigidity, thereby providing that the actual powder stick can be bent only to an immaterial degree during further processing operations thereon or use of the cosmetic pencil incorporating the powder stick, and that resistance to bending accordingly results in a considerable improvement in breaking strength. Furthermore, the comparatively rigid shrink film which is used in accordance with this invention provides that the stick can be formed to a point in a considerably improved fashion, in comparison with previous film-sheathed sticks, as the film used in accordance with this invention is shaved or peeled off in a regular fashion by the sharpening tool for forming the stick to a pointed configuration, and is not torn or roughly chewed off as with previous forms of film.

In accordance with a preferred feature of the invention, the powder stick may be afforded a particularly high degree of protection by the shrink film being in the form of a seamless tube. Such a configuration has the further advantage that the operation of sharpening the powder stick as by a suitable sharpening device is not made more difficult by the presence of a seam, which would give a corresponding change in and more particularly an increase in the wall thickness or gauge of the shrink film tube forming the sheathing.

In accordance with a further preferred feature of the invention, one end of the powder stick, being the front end thereof, is of an at least substantially frustoconical configuration, and there is no shrink film sheathing portion in the region of the frustoconical configuration which thus forms the tip or point of the powder stick. A powder stick of that nature can be used immediately after it has been fitted into a wood casing or other suitable carrier sleeve. In addition, the operation of forming the point or tip on the powder stick is facilitated by the free end edge of the shrink film sheathing, in comparison with a powder stick configuration in which the tip of the powder stick is completely covered by the film. In that case in fact, the shrink film would first have to be cut through and removed by the sharpening tool, over a comparatively large area of the film.

Further in accordance with a preferred feature of the invention, in order to improve the durability and service life of the powder stick, by enhancing its mechanical strength at a part of the stick which may be particularly vulnerable, the rearward end, being the end of the stick which is remote from the tip end, has a chamferred or bevelled or rounded-off edge portion which is covered by the shrink film. The rounded-off or bevelled configuration at the rearward end of the stick and the fact that that part of the stick is additionally covered with the shrink film at least substantially reduces the risk of the powder stick crumbling away at the peripheral edge at the rearward end of the stick, being a part of the stick which is frequently subjected to particularly severe mechanical loadings.

Further objects, features and advantages of the present invention will be more clearly apparent from the following description of a preferred embodiment.

DESCRIPTION OF THE PREFERRED EMBODIMENT

Figure 1:
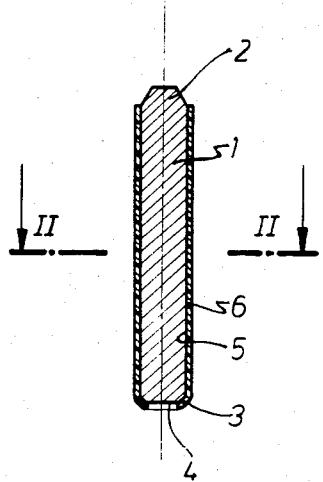
FIG. 1 is a view in longitudinal section taken along line I—I in FIG. 2, of a powder stick in accordance with this invention.
Figure 2:
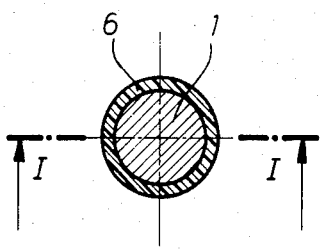
FIG. 2 is a view of the FIG. 1 powder stick in crossection taken along line II—II therein.

Referring therefore now to the drawing, shown therein is a powder stick in accordance with this invention, comprising a core portion 1 which is constituted by the actual powder stick itself which is of any suitable composition and which comprises for example compressed powder which is possibly mixed with one or more other agents such as a binding agent. The powder stick 1 illustrated is of a substantially cylindrical configuration, with its front end, being the end from which powder is applied from the stick 1 on to the skin of the user, being shaped to form a frustoconical configuration as indicated at 2. Provided at the other rearward end of the powder stick core portion 1 is a bevel or chamfer as indicated at 3, which extends around the peripheral edge of the core portion 1, thereby to take away a sharp-edged configuration between a rearward end face 4 of the powder stick and the peripheral surface of the stick as indicated at 5. It will be appreciated that other configurations which remove the sharp-edged configuration as mentioned above may be used instead of the illustrated bevel or chamfer 3, for example a generally rounded-off configuration.

It will be clearly seen from the drawing that the peripheral surface 5 of the core portion 1 of the powder stick is provided with an enclosing sheathing 6 therearound. In accordance with the invention, the sheathing 6 comprises a shrink film or foil of plasticiser-free hard PVC, with a modulus of elasticity of from 2400 to 3000 N/mm$^2$ (in accordance with the German Industrial Standard DIN 53457) (or corresponding US Standard). The thickness of the shrink film forming the sheathing 6 is from about 50 to 200 $\mu$m, while a preferred value in respect of the thickness of the sheathing 6 is of the order of magnitude of about 100 $\mu$m.

The shrink film sheathing 6 is preferably formed by a seamless tube portion. Suitable materials for forming the sheathing 6 include for example those produced by DSG-Schrumpfschlauch GmbH of D-5309 Meckenheim, Federal Republic of Germany, known by the name Deray-H 85. After the shrink operation, the sheathing 6 is comparatively rigid so that it affords good mechanical protection for the core portion 1 of the powder stick. The rigidity of the shrink film sheathing means that the sheathing can also be satisfactorily and easily formed into a substantially pointed tip, at the same time as the powder stick core portion 1 is sharpened, by means of a commercially available sharpening tool or device.

It will be noted in this respect that the frustoconical tip portion 2 of the powder stick is not covered by the shrink film sheathing 6, which thus facilitates the first operation of sharpening the powder stick, while the portion 3 at the rearward end of the stick is in fact covered by the shrink film, thus enhancing the protection afforded thereby.

A powder stick in accordance with the invention as just described above may be manufactured by the core portion 1 first being produced by a suitable forming operation, possibly with pressing or compacting thereof, and drying. The core portion 1 is then introduced into respective tube portions which form the sheathing 6, with the tube portions being of larger diameter than the diameter of the core portion 1.

After the core portion 1 has been fitted into the sheathing 6 in its non-shrunk condition, the core portion 1 together with the sheathing 6 thereon is subjected to a heat treatment at a suitable temperature in a hot air duct; in that operation, very good results are obtained when carrying out the sheathing shrink operation in a hot air flow at a temperature of about 130° C., with the hot air acting on the stick and the sheathing 6 thereon for a period of about 10 seconds. When operating in that way, the surface of the powder stick with sheathing 6 reaches a temperature of about 100° C.

After the sheathing has been shrunk on to the powder stick and the powder stick with sheathing has cooled down at ambient temperature, the powder stick can then be immediately subjected to further processing operations, for example can be introduced into a wood casing or other carrier sleeve member. There is no need for any finishing or dressing operation on the powder stick with sheathing, as the frustoconical tip portion 2 is already formed when the core portion 1 is produced.

As already indicated above, it will be seen more particularly from FIG. 1 that the sheathing 6 does not extend to cover the frustoconical tip portion 2, so that a cosmetic pencil including a powder stick in accordance with this invention is immediately ready for use, and a first sharpening operation only has to be carried out after the powder stick has been used to a fairly considerable extent. As also mentioned above, the operation of re-forming the tip on the cosmetic pencil with the powder stick according to the invention is facilitated by virtue of the nature of the shrink film forming the casing 6. In addition, it will also be seen from FIG. 1 that, as mentioned above also, the sheathing 6 extends over the portion 3 at the rearward end of the core portion 1 of the powder stick, thereby also to provide protection for the powder stick from damage in that region.

It will be appreciated that the above-described embodiment of a powder stick in accordance with this invention has been set forth solely by way of example of the invention which is not restricted thereto. On the contrary, various modifications and alterations may be made in the powder stick without thereby departing from the spirit and scope of the invention.

What is claimed is:

1. A powder stick for a cosmetic pencil, including a lateral sheathing of a shrink film consisting essentially of hard PVC having a modulus of elasticity of from about 2400 to 3000 N/mm$^2$ (in accordance with DIN 53457), with a thickness of from 50 to 200 $\mu$m.

2. A stick as set forth in claim 1 wherein the shrink film sheathing is in the form of a seamless tube portion.

3. A powder stick as set forth in claim 1 wherein the powder stick has a front end forming a tip of substantially frustoconical configuration, said sheathing terminating short of said tip end whereby said frustoconical portion is exposed from the sheathing.

4. A powder stick as set forth in claim 1 wherein said powder stick has a tip end and a rearward end and said rearward end has a peripheral beveled edge which is covered b the shrink film sheathing.

5. A powder stick including a cosmetic powder material which is made into a substantially rigid stick form having a peripheral surface, and an encasing means enclosing said stick form on at least said peripheral surface thereof, the encasing means comprising a shrink film of unplasticized hard PVC with a modulus of elasticity of from about 2400 to 3000 N/mm² (in accordance with DIN 53457), the thickness of said shrink film being from 50 to 200 μm.

6. A powder stick as set forth in claim 5 wherein said shrink film thickness is substantially 100 μm.

* * * * *